United States Patent [19]
Yandell et al.

[11] Patent Number: 5,295,826
[45] Date of Patent: Mar. 22, 1994

[54] DENTAL MIRROR WITH ASPIRATING AND RINSING MEANS

[76] Inventors: Candice A. Yandell; Gregory D. Wiita, both of 624 Sixth Ter., Palm Beach Gardens, Fla. 33418; J. Michael Teets, 5225 SE. Inkwood Way, Hobe Sound, Fla. 33455; Bruce E. Wiita, 848 Lakeside Dr., Palm Beach Gardens, Fla. 33410

[21] Appl. No.: 12,197
[22] Filed: Feb. 2, 1993
[51] Int. Cl.⁵ .......................... A61C 1/00; A61C 3/00; A61B 1/24
[52] U.S. Cl. ........................................ 433/31; 433/30
[58] Field of Search ............... 433/30, 31, 91

[56] References Cited
U.S. PATENT DOCUMENTS

| | | | |
|---|---|---|---|
| 2,436,040 | 2/1948 | Friedman | 433/30 |
| 2,861,342 | 11/1958 | Katz | 433/31 |
| 3,091,034 | 5/1963 | Piscitelli | 433/30 |
| 3,092,910 | 6/1963 | Warriner | 433/31 |
| 3,102,338 | 9/1963 | Warriner | 433/31 |
| 3,884,222 | 5/1975 | Moore | 433/31 X |
| 3,928,916 | 12/1975 | Hansson | 433/31 |
| 4,925,391 | 5/1990 | Berlin | 433/31 |

*Primary Examiner*—Gene Mancene
*Assistant Examiner*—Cindy A. Cherichetti
*Attorney, Agent, or Firm*—Norman Friedland

[57] ABSTRACT

A dental mirror including means for providing suction and rinsing service to the mouth cavity and the like including a substantially annular inlet port formed at the edge of the mirror housing interconnecting longitudinal passages formed in the dental mirror handle and a self-locking swivel coupling connecting the proximal end of the dental mirror handle and a hose or tube connected to a liquid or air and vacuum remotely mounted source. In one embodiment the area of the inlet port progressively increases and in another embodiment the upper and lower plates of the mirror housing are supported by aerodynamically clean struts and the mirror may form the upper plate.

7 Claims, 4 Drawing Sheets

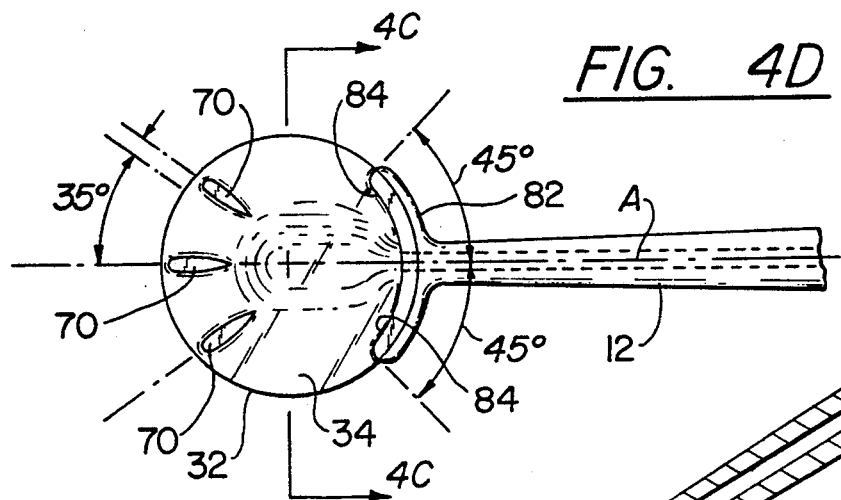
FIG. 4D
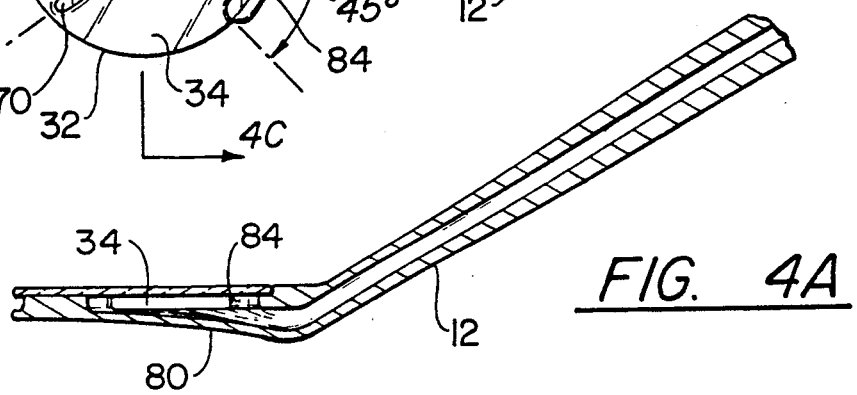
FIG. 4A
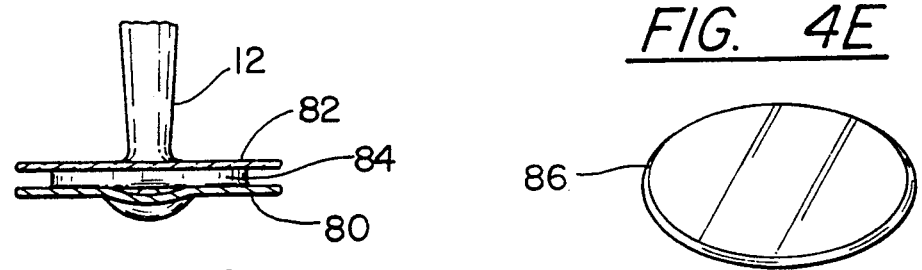
FIG. 4C
FIG. 4E
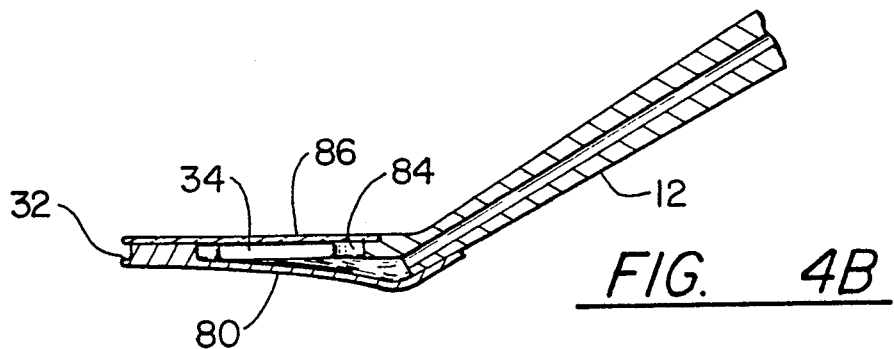
FIG. 4B

DENTAL MIRROR WITH ASPIRATING AND RINSING MEANS

TECHNICAL FIELD

This invention relates to dental mirrors and particularly to the type that includes means for providing aspiration and rinsing capabilities and the construction thereof.

BACKGROUND ART

While there a number of prior art dental mirrors having means for sucking up the mucous, blood, water, particulate, saliva and the like, as well as means for rinsing the mouth area, these prior art devices are either expensive, inefficient and/or are cumbersome to operate. Examples of these types of dental mirrors are disclosed in Warriner U.S. Pat. No. 3,102,338, Hannson U.S. Pat. No. 3,928,916, Katz U.S. Pat. No. 2,861,342 and Berlin U.S. Pat. No. 4,925,391. The Berlin patent, supra, for example, discloses a shaft and mirror combination that includes internal passages extending from the edge of the mirror to the top end of the shaft which includes coupling means for connecting the mirror/shaft combination to a suction source. The edge of the housing of the dental mirror that supports the mirror itself contains a plurality of apertures that are in communication with the interior of the mouth. One of the problems associated with this construction is that these passages are subject to closure if a particle of material, such as metal filling, used by the dentist clogs the aperture or if the dentist allows the edge to touch the walls of the mouth cavity, gums, teeth and the like.

Another class of prior art dental mirrors is concerned with including a light at the mirror itself and the passage means in the handle of the dental mirror for carrying fiber optics or the like from the source of energy to the distal end of the mirror. A number of these prior art devices also include means for conducting fluid to the mirror through the handle for defogging and cleaning the mirror surface. Examples of this class of dental mirrors are disclosed in U.S. Pat. Nos. 4,279,594 granted to Rigutto and 4,629,425 granted to Detsch.

This invention is primarily concerned with the efficiency of the aspirator means in the dental mirror and the construction thereof by including a generally substantially annularly shaped aperture at the edge of the mirror support that communicates with internal passage formed in the mirror handle. In one embodiment the cross sectional area of the annular aperture that forms the inlet port is varied to provide effectual suction capabilities notwithstanding the situation where a portion of the annular aperture may be blocked by an occasional touching of the interior of the mouth. In another embodiment it is contemplated that this invention will incorporate aerodynamically clean vanes or struts for supporting the back plate to the front plate of the mirror support.

Also, this invention contemplates a simplified and economical construction of the dental mirror.

SUMMARY OF THE INVENTION

An object of this invention is to provided and improved dental mirror characterized as having efficient aspiration capabilities and being relatively inexpensive to manufacture without excessively complicating the existing dental mirror.

A feature of this invention is to provide a quasi-annular inlet port at the outer edge of the mirror support housing that has a variable area opening extending around the circumference of the inlet port.

Another feature of this invention is to provide in a dental mirror as described, aerodynamically clean struts supporting the upper and lower plates defining the mirror support housing and in one embodiment the mirror serves as the upper plate.

Another feature of this invention is to provide in a dental mirror as described a swivel fitting for the end of the handle for connecting to a tube or hose for connecting the dental mirror to a remote source of fluid (liquid or air) and a vacuum.

The foregoing and other features of the present invention will become more apparent from the following description and accompanying drawings.

BRIEF DESCRIPTION OF DRAWINGS

FIG. 4A is a partial sectional view of the apparatus depicted in FIG. 4 taken along the longitudinal axis;

FIG. 4B is a partial sectional view identical to FIG. 4A except the back plate is bonded to the handle;

FIG. 4C is a partial view in section taken along lines 4C—4C of FIG. 4D;

FIG. 4D is a top plan view of the apparatus of FIG. 4 with the top plate (mirror) removed;

FIG. 4E is a perspective view of the top plate (mirror);

BEST MODE FOR CARRYING OUT THE INVENTION

While in its preferred embodiment the dental mirror is described as having utility for dental work, as is obvious to one skilled in the art, this type of mirror has utility for viewing other types of cavities.

Figure 1:
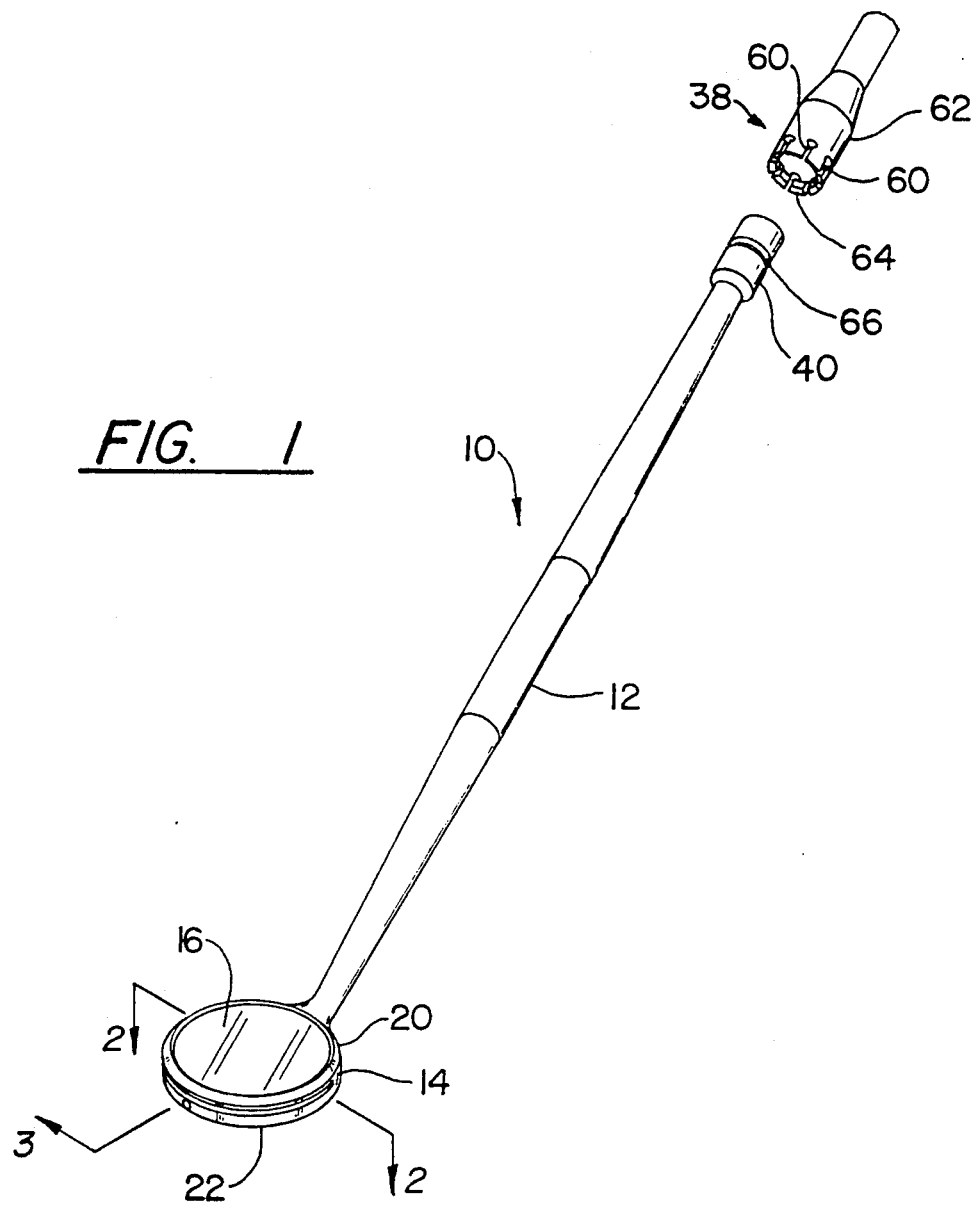
FIG. 1 is a perspective exploded view of the dental mirror with a swivel fitting at the proximal end of the dental mirror.
Figure 2:
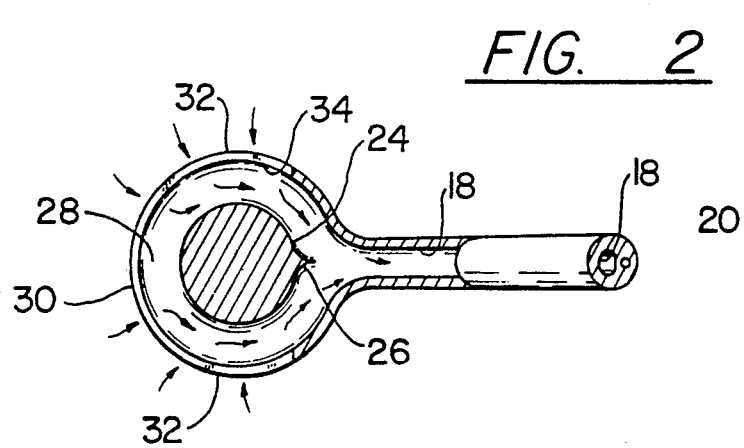
FIG. 2 is a partial view in section taken along lines 2—2 of FIG. 1.
Figure 3:
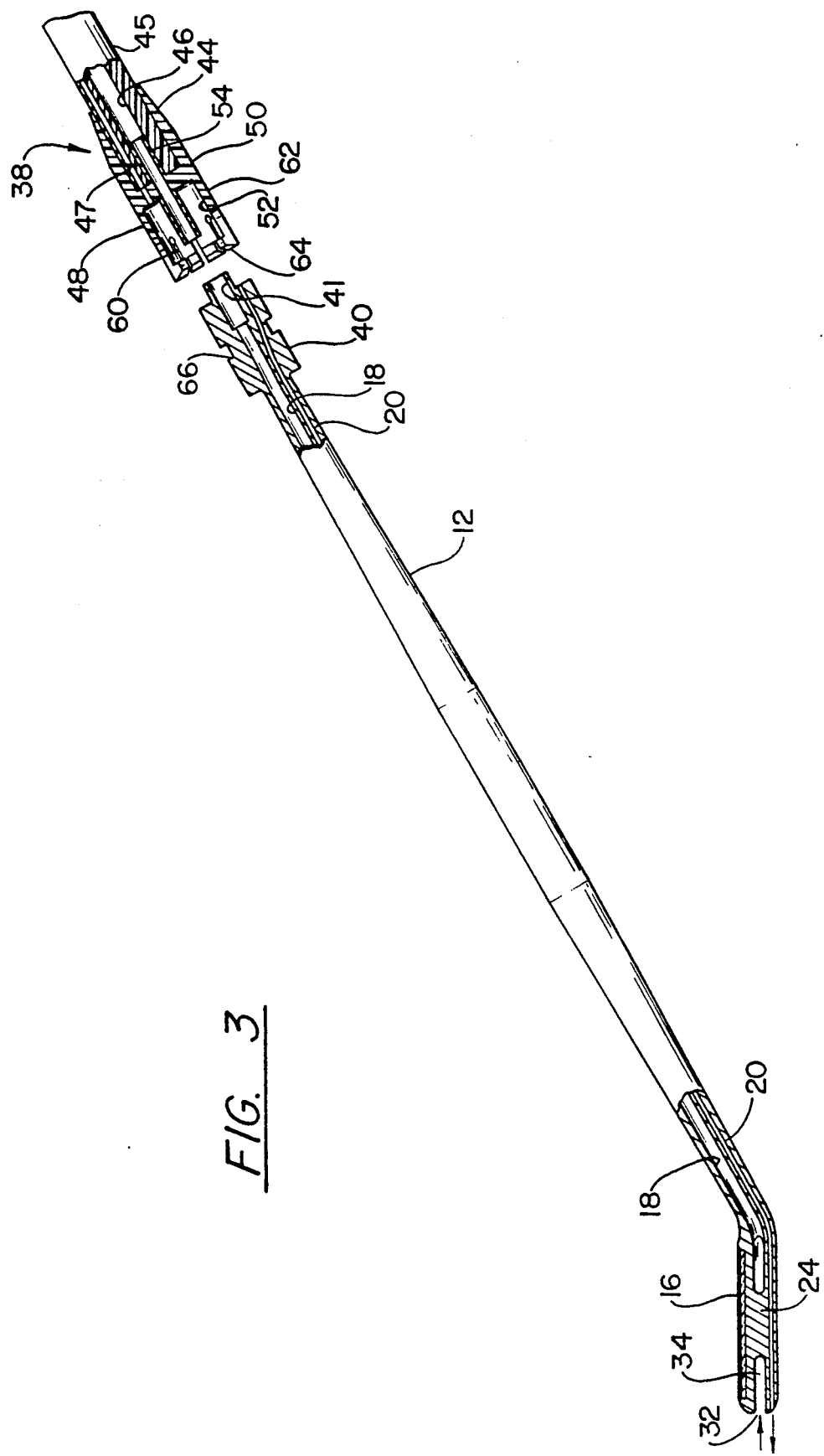
FIG. 3 is a view partly in elevation and partly in section illustrating the details of the swivel fitting and the aspiration and rinsing means of this invention.

As best seen in FIGS. 1, 2 and 3, the dental mirror generally illustrated by reference numeral 10 of this invention, in appearance, looks similar or identical to the customary dental mirror used in most dental practices. It consists of an elongated cylindrically shaped (tubular) handle 12, a mirror housing 14 and mirror 16.

The handle 12 and housing 14 are typically fabricated from a metal such as stainless steel that is susceptible of being autoclave for sterilization purposes. Mirror 16 is typically fabricated from a circular flat plate of glass whose rear surface is suitably coated with a reflective material. In this embodiment, the handle includes a longitudinal passage 18 extending from the proximal end to the distal end of handle 12 of the dental mirror 10 for providing the aspirating service and another smaller diameter longitudinal passage 20 likewise extending the extent of the mirror providing the rinsing service.

As is apparent from viewing these FIGS., the mirror housing basically comprises an upper circular plate having a circular recess for carrying the glass mirror 16 and a lower or back plate 22, both plates being supported by the generally circular member 24 that is either integrally formed or bonded thereto by any suitable means, such as welding or braising. For additional support the circular member 24 may carry diametrically opposing legs 26 and 28 that likewise extend between the upper and lower plates 20 and 22, respectively. The upper plate 20 and lower plate 22 are spaced at all stations of the housing except where leg 28 extends to the outer edge 30 of mirror housing 14.

It is apparent from the foregoing that the upper plate 22 and lower plate 24 at the circumferential extremities define an inlet port 32 extending substantially the circumference of the mirror housing 14 and an annular cavity 34 that communicates with the longitudinal passage. Because the inlet port substantially extends the full expanse of the mirror housing 14, the tendency of blockage is almost non-existing and in the event a potion of the mirror housing touches a portion of the interior of the mouth the blockage occasioned by that touching is almost ineffectual. This construction, demonstrated in recent test, has proven to have exceptionally efficient suction characteristics.

The swivel coupling generally illustrated by reference numeral 38 is adapted to fit a complementary fitting 40 either integrally formed on or bonded to the proximal end of handle 12. As best seen in FIGS. 2 and 3 the coupling 38 consists of an upper hollow end 44 adapted to receive a suitable hose or tube 45 connected to the sources of fluid and vacuum. Hose 45 includes a vacuum passage 46 connected to the lower hollow end 48 of coupling 38 and a rinsing passage 47. Dividing wall 50 separates the upper cavity from the lower cavity 52. Interconnecting tube 54 supported to dividing wall 50 carries open ends on the extremities that are in communication with the suction passage 46 and the longitudinal passage 18. The fitting 40 includes a recess 41 whose outer diameter is sized to accommodate the lower end of tube 54 for assuring a tight fit between the coupling 38 and fitting 44 and minimizing leakage of the vacuum while allowing the coupling 38 to rotate about the longitudinal axis.

Fluid for rinsing or medication can be communicated from the source to the mouth cavity through passage 47 in hose 47 through cavity 52 and the passage 20 in handle 12.

A plurality of longitudinal slits are formed at the lower extremity in the outer wall 62 of coupling 38 to allow flexibility to permit the outer extremity to expand over the outer diameter of fitting 40 so that the annular prongs or inwardly facing ring 64 engages and fits into annular slot 66. This assures rotary motion of coupling 38 while preventing axial movement and hence, preventing the hose from disengaging the handle.

Figure 4:
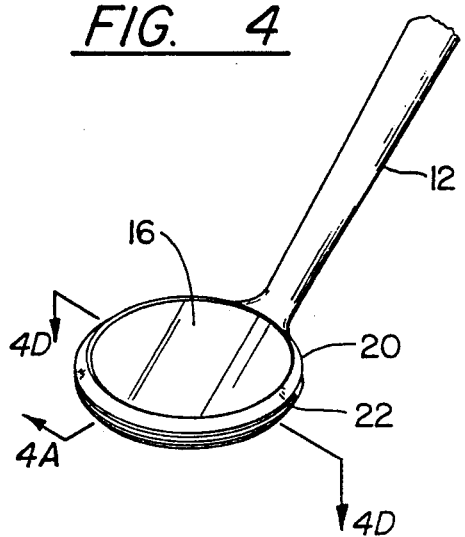
FIG. 4 is a partial view in perspective illustrating another embodiment of this invention.
Figure 5:
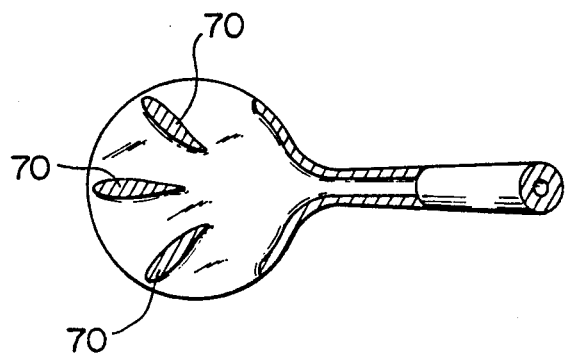
FIG. 5 is a partial view illustrating the details of the annular passage in the mirror portion of the dental mirror with the top plate removed.

FIGS. 4 & 5 exemplify another embodiment of this invention where the upper plate 20 is supported to the lower plate 22 by a plurality of aerodynamic space struts 70. (Like reference numerals in all the FIGS. designate identical or similar parts). While three struts are shown in this embodiment, the number of struts, whether more or less in number will be predicated on the particular design or application. Obviously the number of struts selected will depend on the structural integrity desired. Each strut 70 extends from the upper to the lower plates 20 and 22, respectively.

As noted in FIGS. 4, 4A, 4B, 4C, 4D and 4E, the apparatus can be constructed with basically two (2) or three (3) major component parts. As is exemplified in FIG. 4A, the handle 12 and the back plate 80 are a unitary piece. Struts 70 integrally formed on the upper surface of back plate 80 (FIG. 4D) are located inboard of the inlet port 32 which effectively yields more open suction area and avoids stagnation zones. As shown in FIG. 4D the struts may be positioned such that the center strut is in coincidence with the longitudinal axis A and the adjacent struts are disposed at 35 degrees from the center strut's center line to the adjacent edge of the next adjacent strut.

The base 82 of handle 12 carries a flared arcuate shaped support shoulder 84 depending from the upper surface of base 82 of handle 12 to the height of struts 70 (FIG. 4C) and together therewith serve to support the mirror 86 (FIG. 4E) which defines the upper plate. The span of shoulder 84 will depend on the particular design, but a satisfactory design is where the shoulder is symmetrical relative to the longitudinal axis A and spans 45 degrees from the longitudinal axis on either side of the distal end of said handle.

As is apparent from the foregoing, the back surface of mirror 84 and back plate 80 define the inlet port 32 and the annular cavity 34 and provide a relatively simple construction which virtually is a two component apparatus allowing for a one (1) piece injection welding operation.

FIG. 4B is another construction of the dental mirror depicted in FIG. 4, where the back plate 80 is formed separately from the handle and is bonded thereto, say by welding or braising, but, from a functional standpoint, it is identical.

Figure 7:
FIG. 7 is a sectional view taken along lines 7—7 of FIG. 6.
Figure 8:
FIG. 8 is a sectional view taken along lines 8—8 of FIG. 6.
Figure 9:
FIG. 9 is a sectional view taken along lines 9—9 of FIG. 6.
Figure 10:
FIG. 10 is a sectional view taken along lines 10—10 of FIG. 6.
Figure 11:
FIG. 11 is a sectional view taken along lines 11—11 of FIG. 6.
Figure 6:
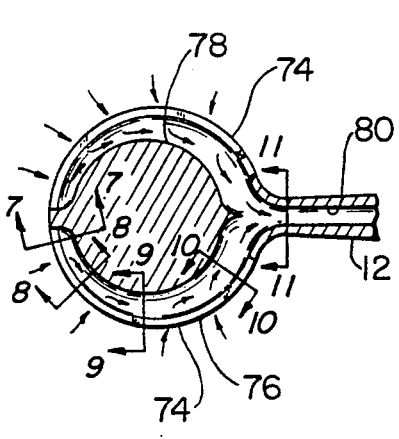
FIG. 6 is another embodiment similar to FIGS. 1 and 4 illustrating a variable area inlet port of the mirror housing.

FIGS. 6 and 7 illustrate another embodiment of this invention where the area of the inlet substantially annular port 74 progressively from the central extremity of the housing 76 increases. This is shown by the cross sections taken along lines A—A, B—B, C—C, and D—D illustrated in FIG. 7. As noted in this embodiment the central circular support member 78 is eccentrically mounted relative to the circular mirror providing the progressively increased area approaching the passage 80 in handle 12. This same feature may likewise be incorporated into the dental mirror configuration exemplified in FIG. 4.

Although this invention has been shown and described with respect to detailed embodiments thereof, it will be appreciated and understood by those skilled in the art that various changes in form and detail thereof may be made without departing from the spirit and scope of the claimed invention.

We claim:

1. A dental mirror apparatus having rinsing and suction capabilities comprising;

an elongated tubular handle having external connection means at the proximal end for connection with a suction or rinsing line, a circular back plate extending at an obtuse angle from the distal end of said elongated tubular handle, a circular mirror coaxially disposed relative to said back plate and spaced therefrom for defining therewith a substantially annular complementary edge extending from one side of said elongated tubular handle to the opposing side of said tubular handle at its distal end where said elongated tubular handle joins said circular back plate and an annular cavity, said complementary edge defining an inlet port extending from one side of said tubular handle to a diametrically opposite side thereof at the distal end of said tubular handle and communicating with said annular cavity for communicating with said external connection means through a passage defined by said tubular handle communicating with said annular cavity, whereby said dental mirror apparatus aspirates and/or rinses the mouth area.

2. A dental mirror apparatus as defined in claim 1 including at least one aerodynamically clean struts disposed adjacent said inlet port and extending from said back plate for supporting said circular mirror.

3. A dental mirror apparatus as claimed in claim 2 wherein said elongated tubular handle and said back plate include a longitudinal axis in coincidence with each other, said aerodynamically clean strut being disposed in coincidence with said longitudinal axis and including at least a pair of other aerodynamically clean struts disposed equally distant on either side of said aerodynamically clean strut.

4. A dental mirror apparatus as claimed in claim 2 including a flared end formed at the distal end of said handle and defining a shoulder substantially extending to the same plane as the top surface of said aerodynamically clean strut for supporting said mirror, said mirror and said back plate defining said annular cavity.

5. A dental mirror apparatus as claimed in claim 4 wherein said flared end extends 45 degrees from said longitudinal axis on either side of the distal end of said elongated tubular handle.

6. A dental mirror as claimed in claim 4 wherein said back plate includes an obtusely disposed end portion complementing the shape of said elongated tubular handle and means for bonding said end portion to said elongated tubular handle.

7. A dental mirror apparatus as claimed in claim 1 wherein said mirror and said back plate include a common central axis, a central support extending from said back plate supports said circular mirror and is eccentrically disposed relative to the central axis of said mirror and back plate such that the area of the annular cavity taken through spaced transverse stations extending from the most forward end of said mirror to the distal end of said handle becomes increasingly larger.

* * * * *